United States Patent [19]

Yokota et al.

[11] Patent Number: 5,227,986
[45] Date of Patent: Jul. 13, 1993

[54] SPECTROMETRIC METHOD FREE FROM VARIATIONS OF ERROR FACTORS

[75] Inventors: Hiroshi Yokota, Izumi; Masaaki Kimura, Hirakata, both of Japan

[73] Assignee: Kurashiki Boseki Kabushiki Kaisha, Kurashiki, Japan

[21] Appl. No.: 639,436

[22] Filed: Jan. 10, 1991

[30] Foreign Application Priority Data

Jan. 11, 1990 [JP] Japan ................................. 2-04042

[51] Int. Cl.⁵ .............................................. G01J 3/02
[52] U.S. Cl. ............................. 364/571.01; 250/339; 364/498
[58] Field of Search ................ 364/571.01, 497, 498, 364/571.03, 571.02, 550, 551.01; 250/339, 352

[56] References Cited

U.S. PATENT DOCUMENTS

| | | | |
|---|---|---|---|
| 4,627,014 | 12/1986 | Lo et al. | 364/571.01 |
| 4,800,279 | 1/1989 | Hieftje et al. | 250/339 |
| 4,805,623 | 2/1989 | Jöbsis | 250/339 X |
| 4,864,842 | 9/1989 | Regimand | 364/571.04 X |
| 4,884,213 | 11/1989 | Iwata et al. | 364/571.01 X |
| 4,959,796 | 9/1990 | Hidaka et al. | 364/497 |

OTHER PUBLICATIONS

"Derivative and Wavelength Modulation Spectrometry", Analytical Chemistry, vol. 51, No. 1, Jan. 1979, 91A.

Primary Examiner—Jack B. Harvey
Assistant Examiner—Edward Pipala
Attorney, Agent, or Firm—Armstrong, Westerman, Hattori, McLeland & Naughton

[57] ABSTRACT

A spectrometric method for determining a physical or a chemical target quantity by performing the photometric measurement at plural wavelengths predetermined which includes the steps of measuring variation vectors by varying error variation factors by predetermined units which are defined in a space having a dimension equal to the number of the plural wavelengths, seeking for a subspace of the space which is orthogonal to all variation vectors, performing the photometric measurement for samples having known values of the target quantity, projecting vectors obtained from the photometric measurement for samples on the subspace and calculating a calibration curve using data obtained by the projection on the subspace.

4 Claims, 9 Drawing Sheets

SPECTROMETRIC METHOD FREE FROM VARIATIONS OF ERROR FACTORS

BACKGROUND OF THE INVENTION

1. Field of the Invention

The present invention relates to a spectrometric method capable of removing error factors.

2. Description of Related Art

Generally speaking, in the spectrometric method for determining a physical or chemical quantity photometric measurement of a target is made at plural wavelengths different from each other and the quantity is determined by a predetermined calibration curve using those data obtained by the photometric measurement.

The calibration curve is usually determined in the following manner.

Assuming the number of wavelengths used for the photometric measurement is n, n or more samples having known with respect to the quantity are prepared and the measurement is performed for all samples prepared. Further, assuming the calibration curve is represented by a linear combination of n photometric data obtained at n wavelengths in the following form;

$$b = Q_1 B_1 + Q_2 B_2 + \ldots + Q_n B_n$$

wherein b indicates the quantity to be determined, $B_1$ to $B_n$ are photometric data obtained at n wavelengths and $Q_1$ to $Q_n$ are coefficients, these coefficients are determined according to a known approximation method such as least square method so that the sum of differences $\Delta b_i$ for $i=1$ to n each of which is defined as a difference between each of known values of the quantity and each of values thereof calculated according to the above equation can be minimized.

Once the calibration curve has been determined, the quantity of an unknown sample is calculated from the calibration curve using n photometric data at n wavelengths obtained with respect to the unknown sample.

Photometric data obtained include various errors. According it is necessary to remove those errors in order to obtain a correct value. As factors which cause those errors, temperature variation of the sample (hereinafter referred to as sample temperature variation), variation of the scattering factor of the sample (hereinafter referred to as sample scattering variation) and temperature variation of the measuring apparatus (hereinafter referred to as machine temperature variation) can be recited.

In order to remove errors due to the sample, measured data are corrected according to the temperature of sample measured at that time. Also, it is necessary to maintain the temperature of sample constant in order to avoid a rise of the temperature of sample due to the incident light during the measurement.

However, there may be a shift between the measured temperature and an actual temperature of sample and, also, there may be a difference between the temperature of a portion of the sample at which it is measured and the temperature of another portion thereof at which the photometric measurement is performed actually. Further, the spectrometer becomes more complicated and higher at the cost thereof in order to control the temperature of sample constant and, generally speaking, the temperature control itself is quite difficult.

In order to eliminate errors due to temperature drifts of the light source and sensors used in the spectrometer, data can be corrected according to changes in temperatures of them in a manner similar to the correction of errors due to the sample temperature variation and it is desirable to control the machine temperature in the spectrometer.

However, this is also quite difficult as in the case of the control of the sample temperature.

Further, for instance, the two wavelength spectrometry is used in order to eliminate errors caused by the sample scattering variation due to inhomogeneousness of the sample such as muddiness.

In this method, the measurement is performed using two lights of different wavelengths $\lambda_1$ and $\lambda_2$ to obtain a difference $\Delta A$ between two absorbances $A(\lambda_1)$ and $A(\lambda_2)$ measured. If two wavelengths $\lambda_1$ and $\lambda_2$ are near with each other in the case of the sample having muddiness therein, errors due to the sample scattering variation are considered to be substantially equal between two wavelengths $\lambda_1$ and $\lambda_2$. Accordingly, the difference of absorbance $\Delta A$ can be considered free from errors due thereto. Therefore, the determination of the quantity free from those errors can be made by using a calibration curve obtained from data regarding the difference of absorbances $\Delta A$.

Further, in the differential spectrometry, a calibration curve is determined using differential absorbance $\Delta A$ obtained when the difference between two wavelength $\lambda_1$ and $\lambda_2$ is made close to zero. In this method, it is possible to remove errors due to the sample scattering variation which has no wavelength dependency.

However, in the known method such as the two wavelength spectrometry or the differential spectrometry, only the sample scattering variation with no wavelength dependency can be removed. In fact, the sample scattering varies with the wavelength as in Rayleigh scattering. Accordingly, it is impossible to remove errors due to the sample scattering variation completely.

SUMMARY OF THE INVENTION

An essential object of the present invention is to provide a spectrometric method being capable of removing various errors included in measured data effectively.

In the spectrometry according to the present invention, the following steps S1 to S4 are performed.

S1; measuring an output variation per unit of each of error factors beforehand at every wavelength, S2; determining a subspace orthogonal to all vectors in a space of a dimension equal to the number of wavelengths used for the measurement which are obtained by assuming that data of output variations obtained form vectors in said space, S3; performing spectral measurements for plural samples having known physical or chemical quantities of a target of measurement at respective wavelengths and converting data obtained to those projected on said subspace, and S4; determining a calibration curve representing a correlation of the quantity to be determined with data obtained by the above conversion.

According to the present invention, all factors causing errors are removed effectively since the calibration curve is determined based on data projected on said subspace orthogonal to all vectors corresponding to all error factors.

Data measured with respect to unknown samples are projected in said subspace and the target quantity is determined from the projected data according to the calibration curve.

BRIEF DESCRIPTION OF THE DRAWINGS

These and other objects and features of the present invention will become clear from the following description taken in conjunction with the preferred embodiment thereof with reference to the accompanying drawings, in which.

DETAILED DESCRIPTION OF THE PREFERRED EMBODIMENT

Figure 1A:
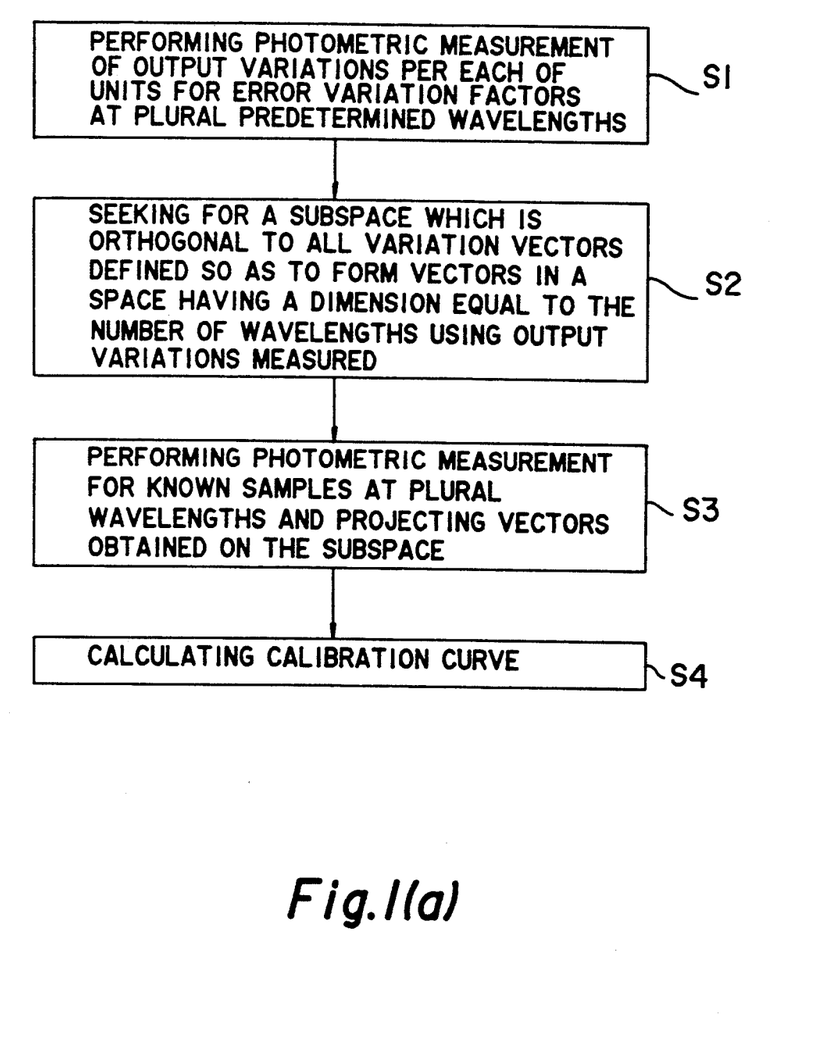
FIG. 1(a) is a flow chart for determining a calibration curve according to the present invention.
Figure 1B:
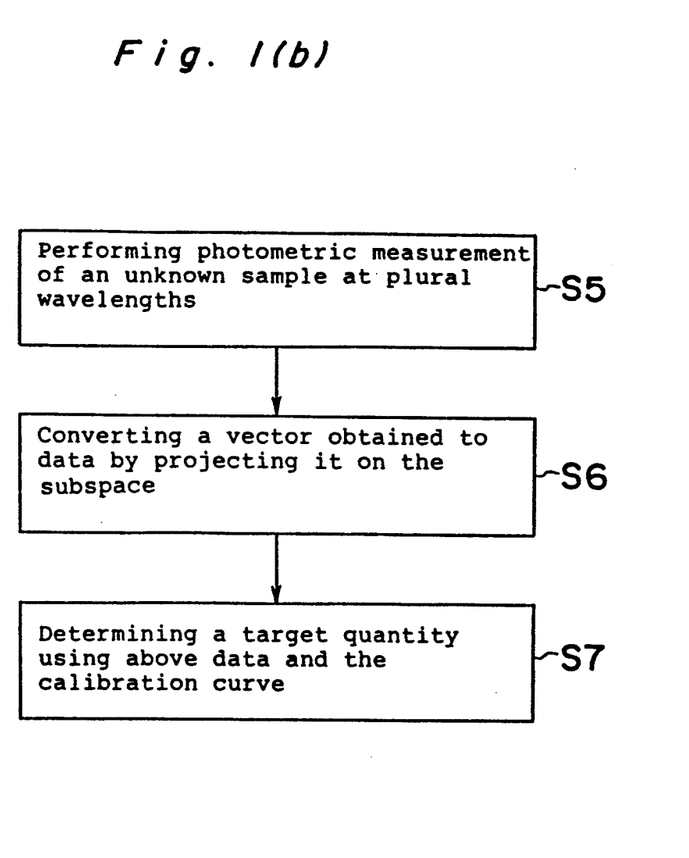
FIG. 1(b) is a flow chart for determining the target quantity according to the calibration curve.
Figure 2:
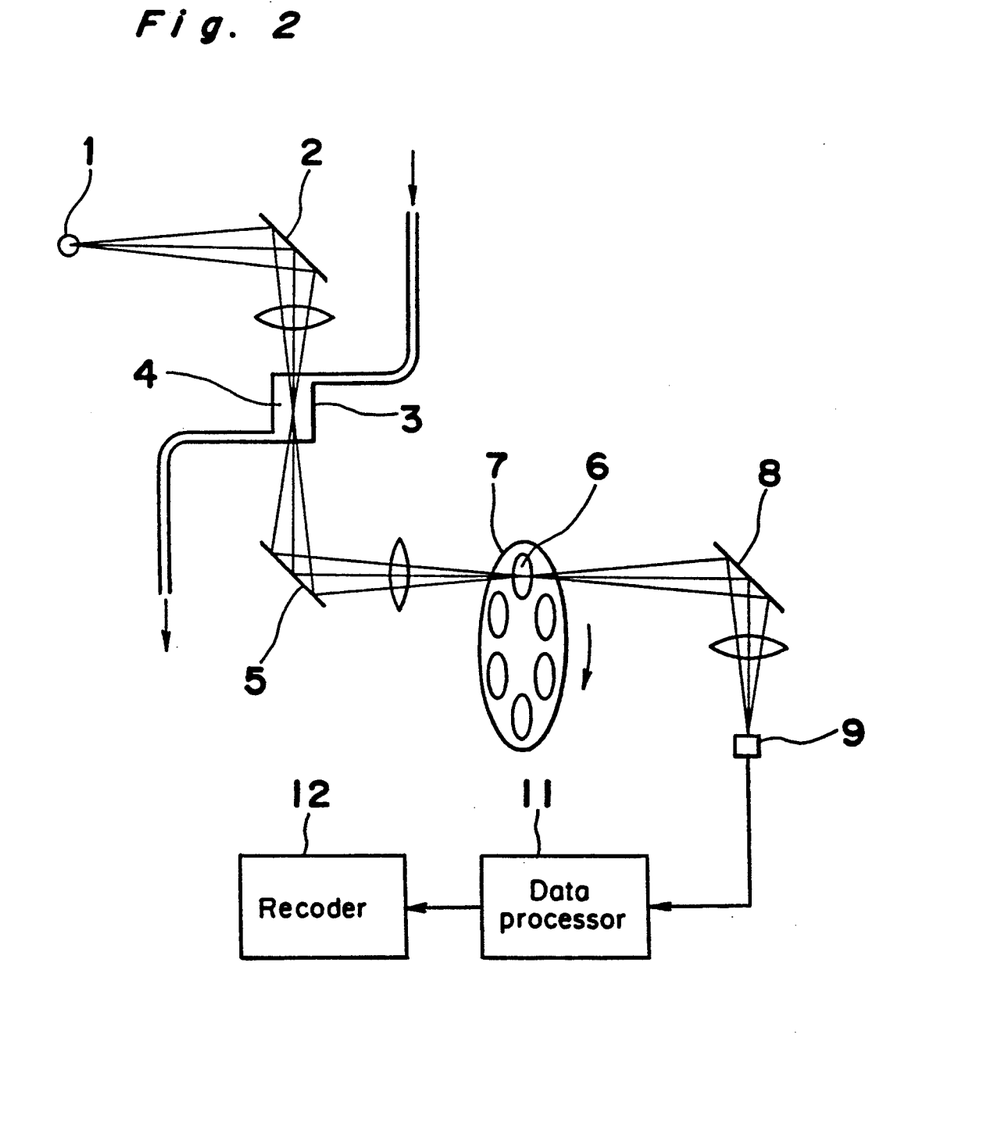
FIG. 2 is a schematical view for showing a composition of an apparatus for measuring infrared rays transmitted through a sample.

FIG. 2 shows a schematical composition of an apparatus for measuring transmitted infrared rays. The measurement of the density in this apparatus is based upon Beer-Lambert Law wherein a near infrared transmitted spectrum of a target liquid varies proportional to the density of a component contained in the target liquid.

In this apparatus, infrared rays emitted from a light source 1 are reflected by a reflection mirror 2 and, then, are focused in a flow cell 3. A sample liquid 4 is introduced into the flow cell 3 continuously. The infrared rays having been transmitted through the sample 4 are reflected by a reflection mirror 5 and, then, are decomposed into rays of predetermined wavelengths by six interference filters 6. These interference filters 6 are supported radially by a disc 7 and it is rotated at 15 turns per second by a rotating means not shown. The light having been transmitted through one of six filters 6 is reflected by a reflection mirror 8 and, then, focused on a light sensor 9. The sensor 9 transforms an incident light signal to an electric signal. A data processor 11 converts each electric signal from the sensor 9 to digital data and determines respective absorbances Ai (i=1 to 6) about six wavelengths corresponding six filters 6 according to the next equation with use of blank data.

$$Ai = -\log(Ii/Ioi) \quad (1)$$

wherein Ai indicates the absorbance at i-th wavelength, Ii and Ioi indicate intensities of lights transmitted through cell filled with the sample and the blank cell at i-th wavelength, respectively.

According to Beer-Lambert Law, the following equation is obtained.

$$Ai = a_i \cdot b \cdot c \quad (2)$$

wherein $a_i$ is the absorption coefficient of a material at i-th wavelength, b is a cell length and c is a density of a sample. Since $a_i$ takes a proper value according to the material and the cell length b is constant, a product $k_i$ of $a_i$ and b is considered to be constant. Accordingly, the equation (2) is set as follows.

$$Ai = k_i \cdot c \quad (b\ 3)$$

Therefore, if $k_i$ is determined beforehand by another measurement, the density c can be determined by measuring the absorbance Ai. Data processed by the data processor 11 are outputted to a recorder 12.

The light intensity Ii detected by the sensor 9 varies according to not only the sample density $c_i$ but also the sample temperature, the sample scattering and the temperature of the apparatus.

Figure 3:
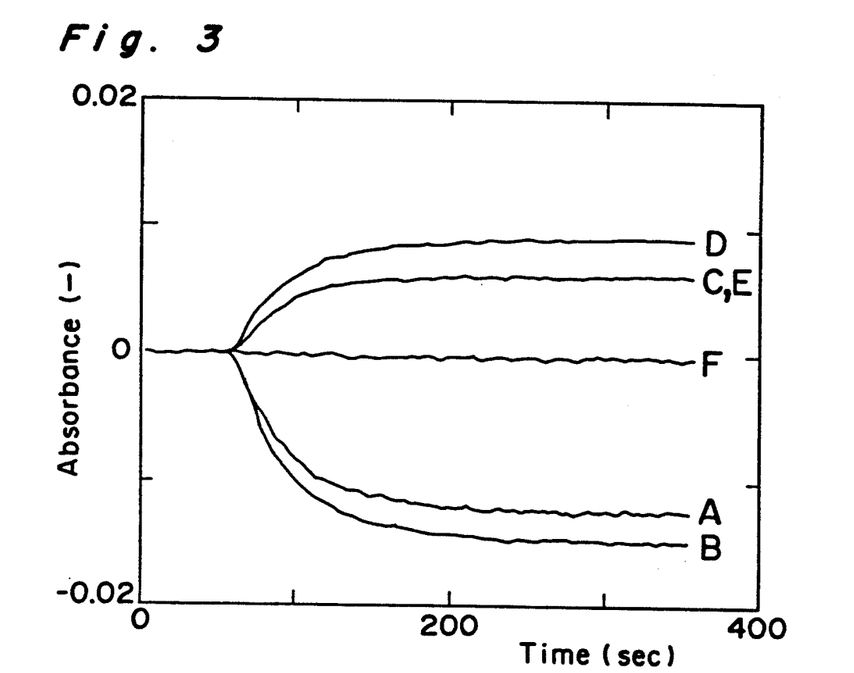
FIG. 3 is a graph for showing an output variation due to the sample temperature variation.

FIG. 3 shows variations of the absorbance of water due to the sample temperature variation at six wavelengths 1530 nm (A), 1400 nm (B), 1430 nm (C), 1490 nm (D), 1550 nm (E) and 1680 nm (F) when the temperature varies form 23.0° C. to 27.5° C.

Figure 4:
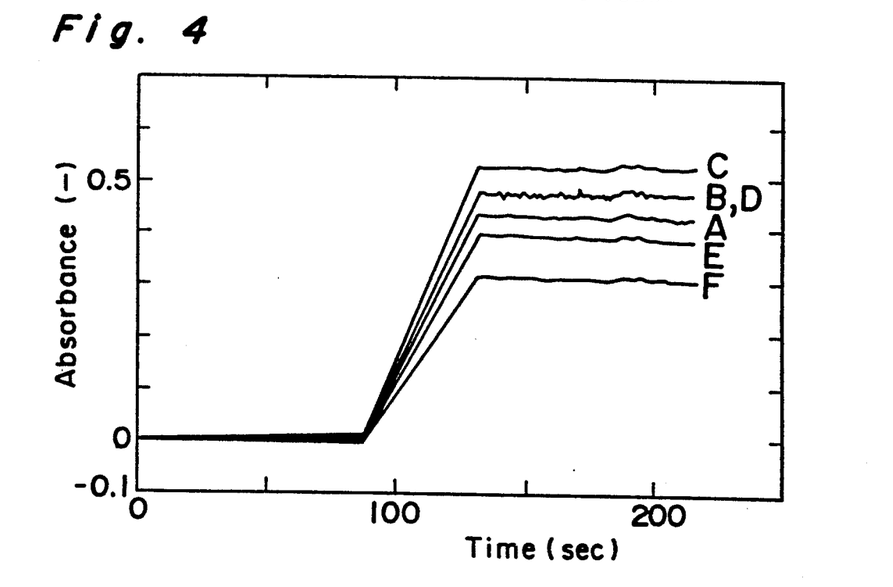
FIG. 4 is a graph for showing an output variation due to the sample scattering variation.

Similarly to FIG. 3, FIG. 4 shows variations of the absorbance of water at six wavelengths when milk of a predetermined amount is added to the water to make it cloudy in white.

According to the conventional method, a calibration curve represented by the following equation is determined using six output values Ai as they are.

$$\begin{aligned} c &= Q_1 A_1 + Q_2 A_2 + \ldots + Q_6 A_6 + \\ &\quad Q_7 A_1^2 + \ldots + Q_{12} A_6^2 \\ &= g(Ai) \end{aligned} \quad (4)$$

wherein Qj (j=1 to 12) are coefficients to be determined so as to minimize errors. In this method, the density determined by the above calibration curve is affected by various error factors directly.

According to the present invention, output data Ai (i=1 to 6) at six wavelengths are converted into data free from those error factors in the following manner.

At first, output variations $\Delta A_1, \Delta A_2, \ldots, \Delta A_6$ per a unit of the sample temperature at the six wavelengths are measured and represented by a vector $\bar{T}$ having six components $\Delta A_1$ to $\Delta A_6$ which is defined in a space having a dimension equal to the number of wavelengths used for the measurement.

$$\bar{T} = (\Delta A_1, \Delta A_6)$$

Similarly, output variations per individual units due to the sample scattering variation (S) and the machine temperature variation (M) are represented by vectors $\bar{S}$ and $\bar{M}$.

Then, a vector $\bar{P}$ which satisfies the following equations is sought for.

$$\vec{P} \cdot \vec{T} = 0$$

$$\vec{P} \cdot \vec{S} = 0$$

$$\vec{P} \cdot \vec{M} = 0 \quad (5)$$

wherein "·" indicates the inner product of two vectors.

In this case, three vectors $\vec{P}_1$, $\vec{P}_2$ and $\vec{P}_3$ exist as independent solutions of the vector $\vec{P}$. These three independent vectors $\vec{P}_1$, $\vec{P}_2$ and $\vec{P}_3$ defines a subspace of the whole space with six dimension. This subspace is orthogonal to all vectors $\vec{T}$, $\vec{S}$ and $\vec{M}$.

Next, the measurement is performed for known samples of a number equal to or more than the number of dimension of said subspace at the six wavelengths. Data thus obtained are converted to data free from the error factors by projecting the former on said subspace in the following manner.

Assuming each set of six data $A_1$ to $A_6$ of one sample measured at six wavelength, respectively is represented by a vector $\vec{A}$ having a dimension equal to the number of the wavelengths used for the measurement, the latter data can be obtained by taking inner products as follows.

$$X_1 = \vec{P}_1 \cdot \vec{A}$$

$$X_2 = \vec{P}_2 \cdot \vec{A}$$

$$X_3 = \vec{P}_3 \cdot \vec{A} \quad (6)$$

Namely, $X_1$, $X_2$ and $X_3$ are data obtained by projecting the vector $\vec{A}$ on said subspace defined by three independent vectors $\vec{P}_1$, $\vec{P}_2$ and $\vec{P}_3$ and, accordingly, free from the error factors mentioned above.

Figure 5:
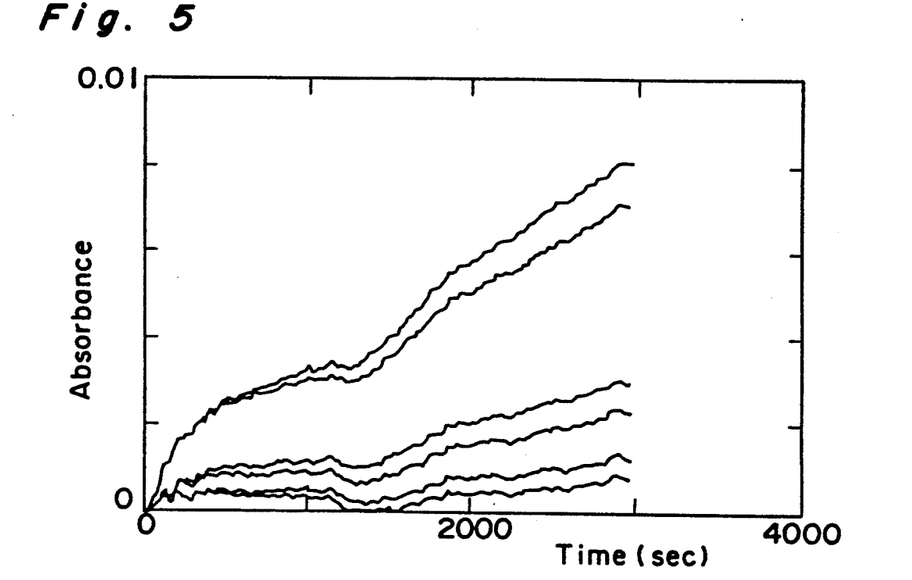
FIG. 5 is a graph for showing a variation of the absorbance of a sample.
Figure 6A:
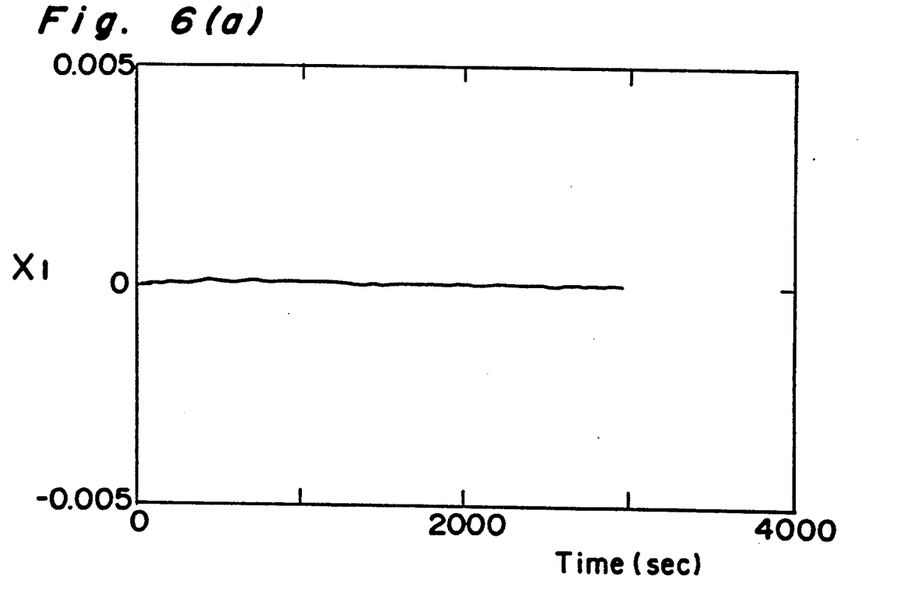
FIGS. 6(a), 6(b) and 6(c) are graphs for showing variations of data projected on the subspace defined according to the present invention, respectively.
Figure 6B:
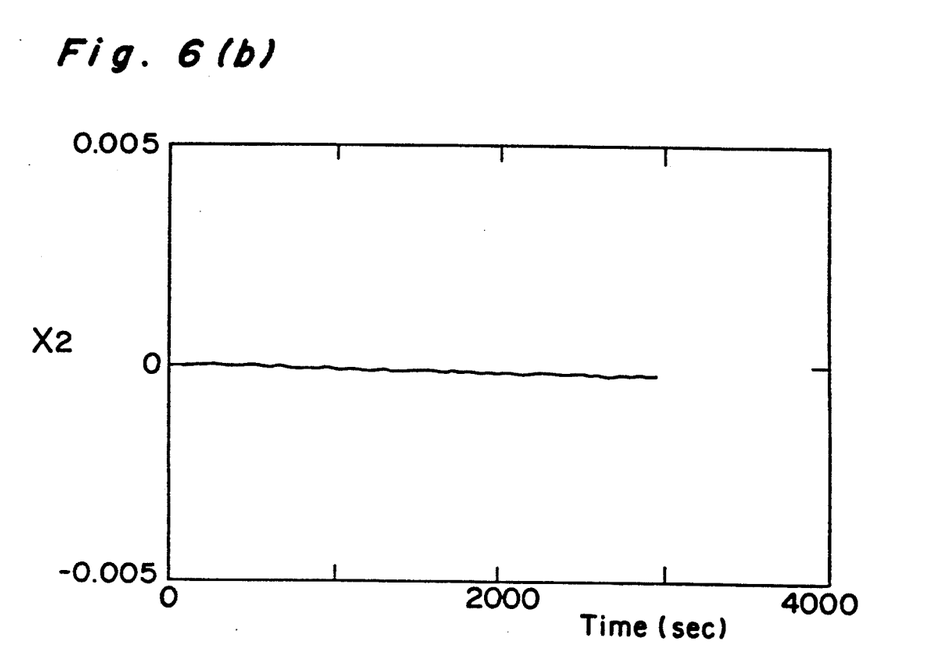
Figure 6C:
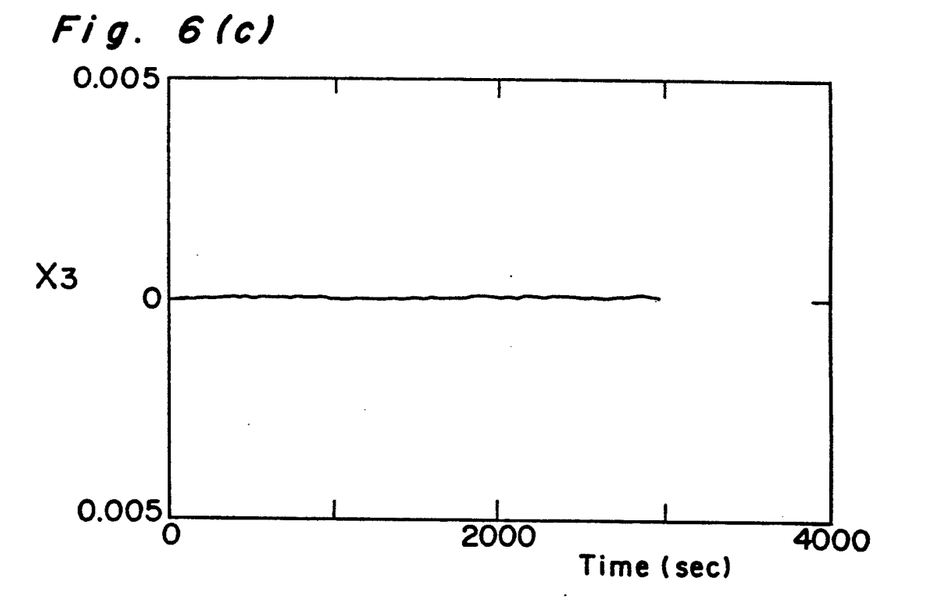

FIGS. 6(a), 6(b) and 6(c) show variations of three data $X_1$ to $X_3$, respectively, when the absorbances of the sample at six wavelengths are varied as shown in FIG. 5. As is apparent from these figures, all of three data are kept constant.

Then, Coefficients $R_j$ of the calibration curve for the density c are determined using all of sets $X_1$, $X_2$ and $X_3$ obtained from all samples. The calibration curve c is assumed to be a polynominal comprised of singlenominals and binominals of $X_1$ to $X_3$ as follows.

$$c = R_1 X_1 + R_2 X_2 + R_3 X_3 + R_4 X_1^2 + R_5 X_2^2 + R_6 X_3^2 = f(x_i) \quad (7)$$

As is well known to those skill in the art, the coefficients $R_j$ (j=1 to 6) can be determined by a known approximation method, for example, least square method.

Upon determining the density of an unknown sample, said six output values $A_i$ (i=1 to 6) are measured at six wavelengths with respect thereto and the vector consisted of said six values is projected on said subspace to obtain data $X_i$ (i=1 to 3). Thereafter, the density c is determined using said calibration curve.

As will be stated in detail, according to the present invention, the accuracy of measurement is enhanced amazingly when compared with the conventional method.

EXAMPLE I

Measurement of Ethanol During the Brewing Process of Japanese "Sake"

Wavelength used for the measurement are 2044, 2126, 2279, 2301, 2339 and 2392 (nm), respectively, the scattering variation vector $\vec{S}$(measured values) is (1.23, 1.21, 1.15, 1.11, 1.02, 1.00) and the machine temperature variation vector $\vec{M}$ is (1, 1, 1, 1, 1, 1). In this case, errors due to the machine temperature variation are assumed to have no wavelength dependency and errors due to the sample temperature variation are neglected. Four base vectors $\vec{P}_1$, $\vec{P}_2$, $\vec{P}_3$ and $\vec{P}_4$ orthogonal to the vectors $\vec{S}$ and $\vec{M}$ as follows.

$\vec{P}_1 = (-0.3982, -0.0569, 0.3698, 0.3698, 0.3698, -0.6542)$ $\vec{P}_2 = (0.3122, -0.7374, 0.3454, 0.3455, -0.3388, 0.0731)$ $\vec{P}_3 = (-0.1924, 0.0186, 0.7386, -0.6269, -0.0745, 0.1365)$ $\vec{P}_4 = (-0.5243, 0.3292, 0.1097, 0.4268, -0.5975, 0.2561)$ Accordingly, four projected data $X_1$ to $X_4$ are obtained from an observation vector $\vec{A}$ consisted of six components $A_1$ to $A_6$ measured at six wavelengths {$\vec{A}$ consisted of six components $A_1$ to $A_6$ measured at six wavelengths {$\vec{A} = (A_1, A_2, A_3, A_4, A_5, A_6)$} as follows.

Figure 7:
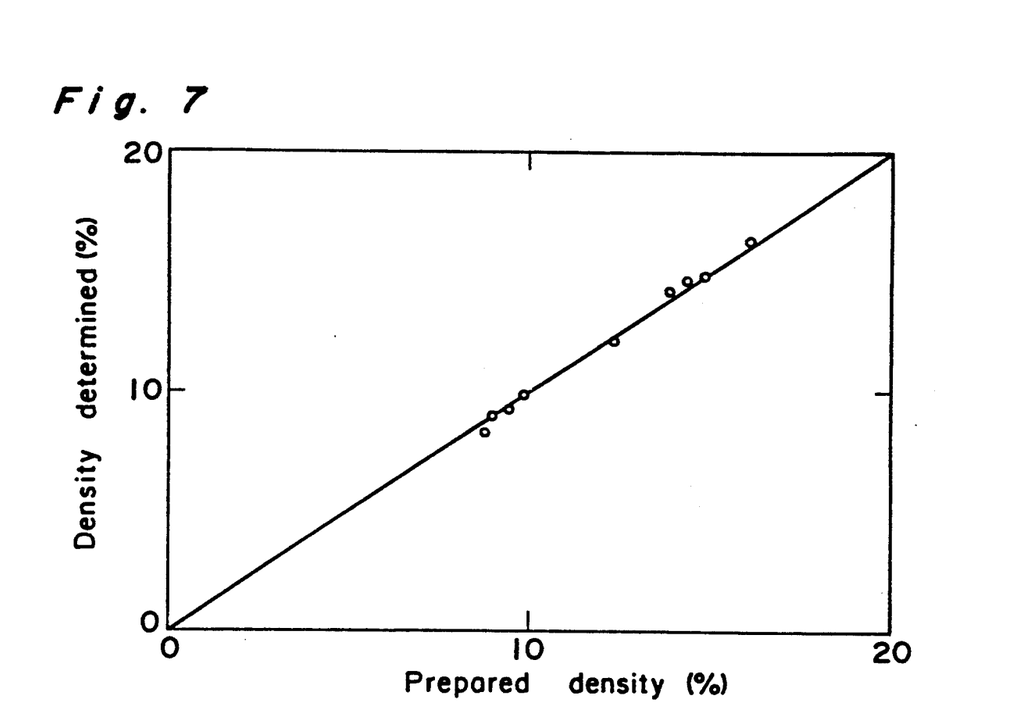
FIG. 7 is a graph showing densities of ethanol calculated using the calibration curve determined according to the present invention.

$X_1 = \vec{P}_1 \cdot \vec{A}$
$X_2 = \vec{P}_2 \cdot \vec{A}$
$X_3 = \vec{P}_3 \cdot \vec{A}$
$X_4 = \vec{P}_4 \cdot \vec{A}$ FIG. 7 shows densities which are calculated using the following calibration curve in comparison with real densities prepared beforehand.

$$c = R_1 X_1 + R_2 X_2 + R_3 X_3 + R_4 X_4 \quad (8)$$

wherein c indicates the density of ethanol and $R_i$ (i=1 to 4) are coefficients to be determined.

Figure 8:
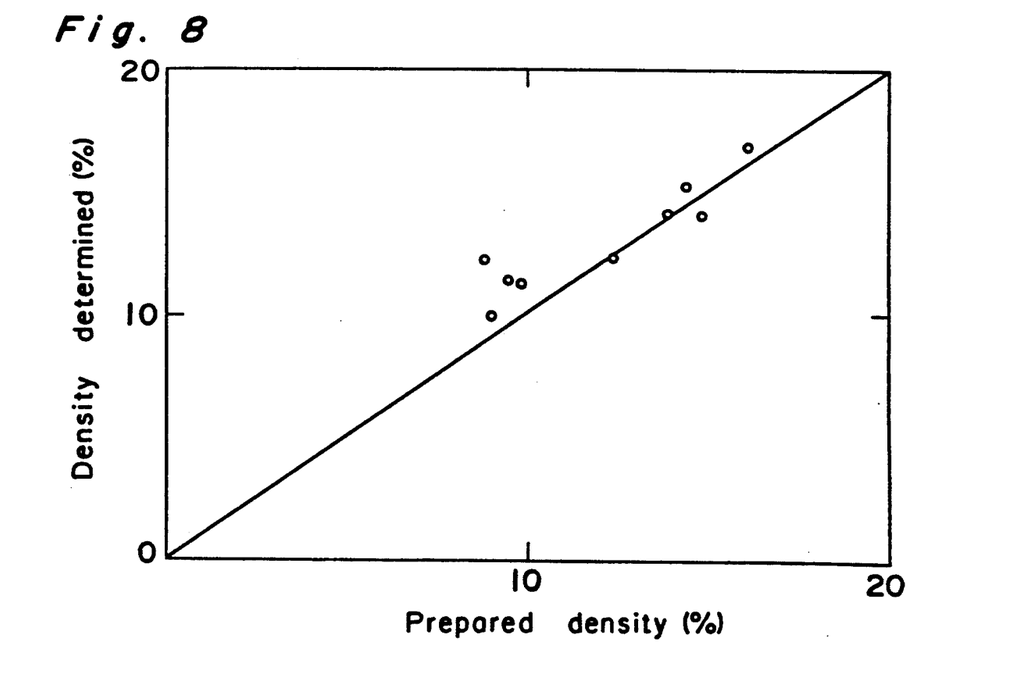
FIG. 8 is a graph showing densities of ethanol calculated using a calibration curve determined according to the conventional spectrometry.

FIG. 8 shows densities which are calculated using the following conventional calibration curve in comparison with real densities.

$$c = Q_1 A_1 + Q_2 A_2 + \ldots + Q_6 A_6 \quad (9)$$

Table shows all data shown in FIGS. 7 and 8 which are obtained with respect nine samples.

As is apparent from comparison of FIG. 7 with FIG. 8, the accuracy of measurement is greatly improved in the present invention.

| Sample No. | Real density | Present invention | Conventional method |
| --- | --- | --- | --- |
| 1 | 16.12 | 16.30 | 16.82 |
| 2 | 14.86 | 14.83 | 14.05 |
| 3 | 14.39 | 14.62 | 15.21 |
| 4 | 13.92 | 14.21 | 14.06 |
| 5 | 12.39 | 12.06 | 12.25 |
| 6 | 9.87 | 9.82 | 11.23 |
| 7 | 8.83 | 8.36 | 12.14 |
| 8 | 9.03 | 8.98 | 9.91 |
| 9 | 9.49 | 9.26 | 11.31 | unit weight %

EXAMPLE II

Removement of Errors Due to Temperature Variation in Measurement of Density of Sulfuric Acid Wavelengths used for the measurement are 980, 1080, 1150, 1200, 1250 and 1300 (nm), the sample temperature variation vector $\vec{T}$ is measured (2.27, −0.53, 5.53, −1.56, −3.80, −1.15) and the machine temperature variation vector $\vec{M}$ is (1, 1, 1, 1, 1, 1,). It is assumed that errors due to the machine temperature variation have no temperature dependence and that errors due to the sample scattering variation are neglected. Four base vectors $\vec{P}_1$, $\vec{P}_2$, $\vec{P}_3$ and $\vec{P}_4$ being independent with each other and orthogonal to both vectors $\bar{T}$ and $\bar{M}$ are obtained as follows.

$\bar{P}_1 = (-0.3800, -0.0855, 0.3736, 0.3736, 0.3736, -0.6554)$
$\bar{P}_2 = (-0.5655, 0.7129, 0.0732, 0.0732, -0.3899, 0.0961)$
$\bar{P}_3 = (-0.0991, 0.2654, 0.1759, -0.7973, -0.5010, -0.0458)$
$\bar{P}_4 = (-0.5239, -0.4893, 0.3434, -0.0086, 0.0764, 0.6019)$ Using the observation vector $A = (A_1, A_2, A_3, A_4, A_5, A_6)$ obtained at six wavelengths, the following projected values $X_1$ to $X_4$ are obtained.

$X_1 = \bar{P}_1 \cdot \bar{A}$
$X_2 = \bar{P}_2 \cdot \bar{A}$
$X_3 = \bar{P}_3 \cdot \bar{A}$
$X_4 = \bar{P}_4 \cdot \bar{A}$ Using projected values, the following calibration curve c representing the density of sulfuric acid is determined.

$$c = R_1 X_1 + R_2 X_2 + R_3 X_3 + R_4 X_4 \tag{10}$$

Figure 9:
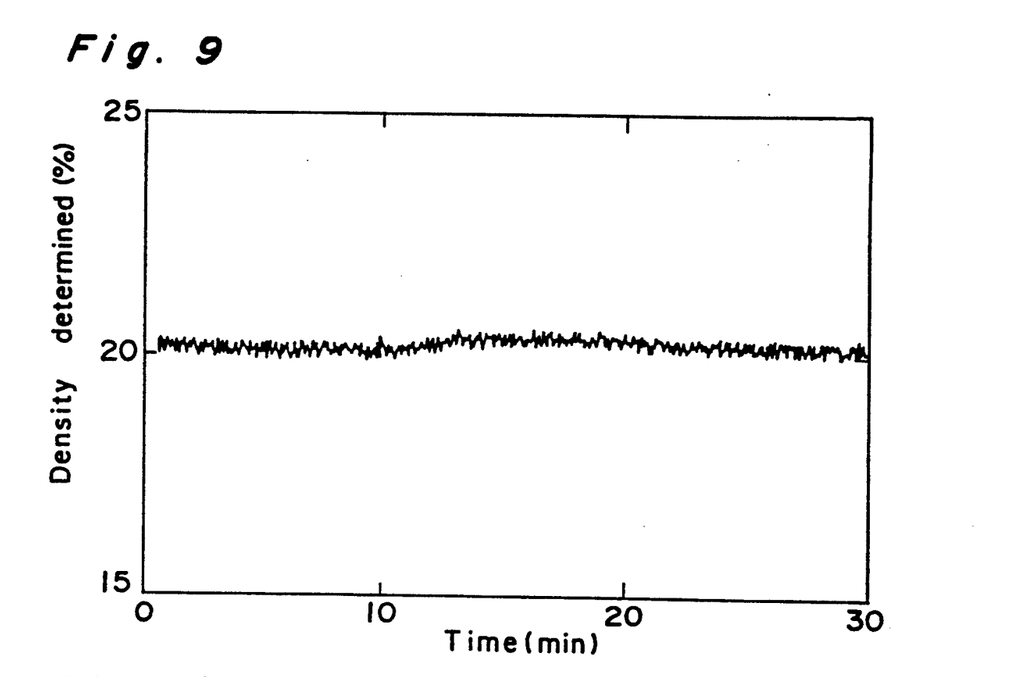
FIG. 9 is a graph showing densities of sulfuric acid calculated using the calibration curve determined according to the present invention.

FIG. 9 shows a time variation of the density c calculated using the calibration curve according to the present invention.

Figure 10:
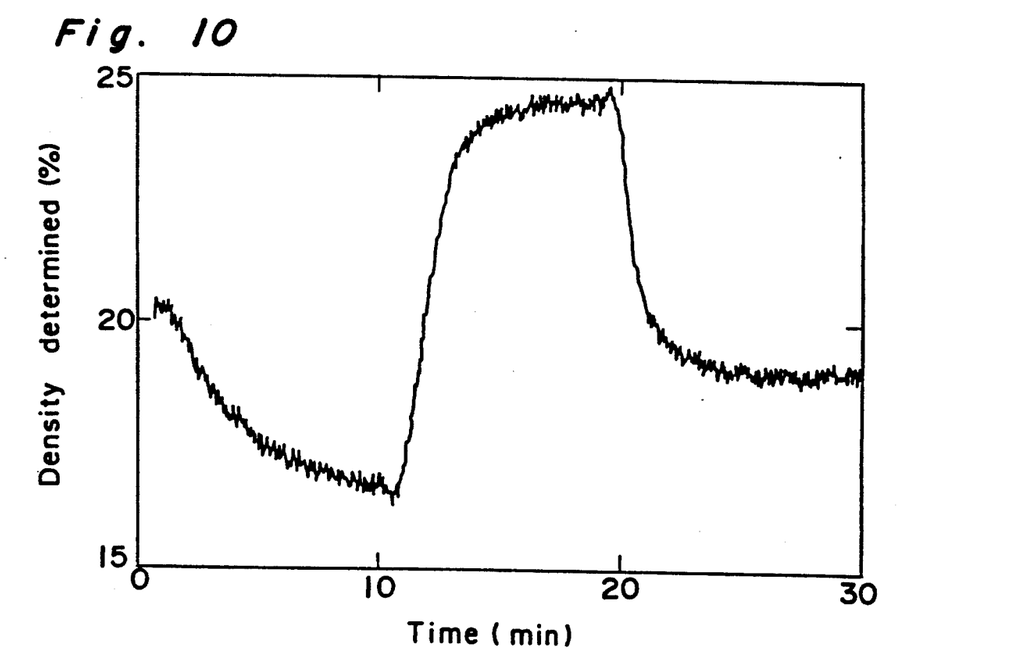
FIG. 10 is a graph showing densities of sulfuric acid calculated using the calibration curve determined according to the conventional spectrometry.

FIG. 10 shows a time variation of the density calculated using the conventional calibration curve in a form as follows.

$$c = Q_1 A_1 + Q_2 A_2 + \ldots + Q_6 A_6 \tag{11}$$

Figure 11:
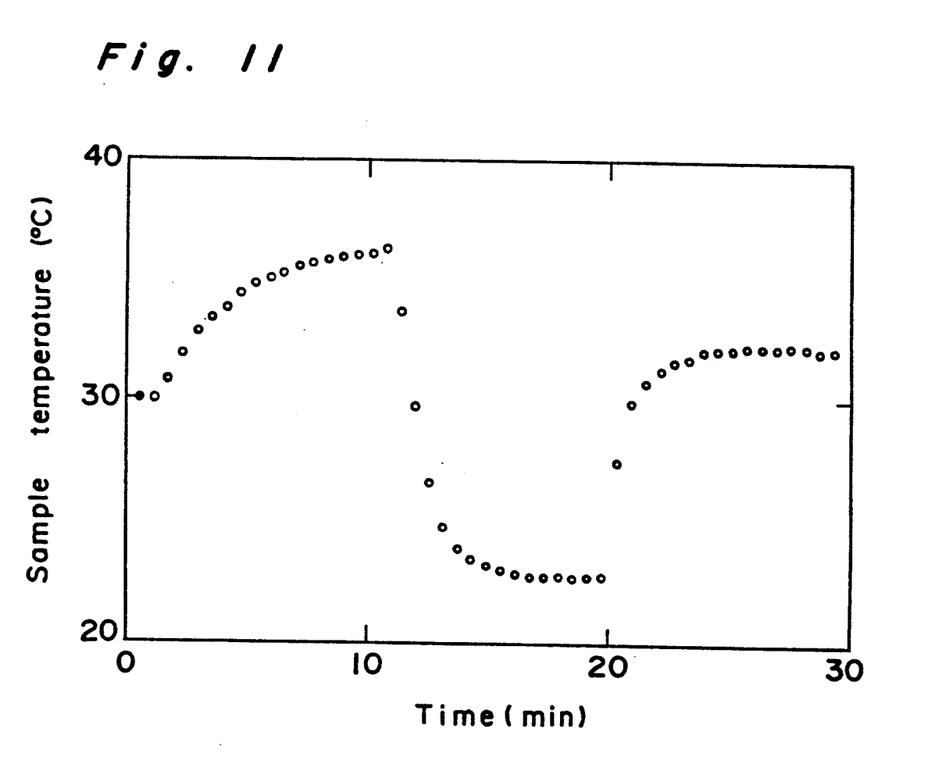
FIG. 11 is a graph showing a sample temperature variation during the measurement of data shown in FIG. 9 and FIG. 10.

Further, FIG. 11 shows a time variation of the sample temperature during the measurement. As is apparent from comparison of FIG. 9 with FIG. 10, the density according to the present invention is quite stable having a very small amplitude while the density according to the conventional method varies according to the variation of the sample temperature shown in FIG. 11 significantly. Thus, in the present preferred embodiment, errors due to the variation of the sample temperature are perfectly removed.

In the preferred embodiment, the density is used as a physical or chemical quantity, but other physical or chemical quantities can be sought for by using a calibration curve determined according to the present invention.

It is understood that various other modifications will be apparent to and can be readily made by those skilled in the art without departing from the scope and spirit of the present invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art to which the present invention pertains.

What is claimed is:

1. Spectrometric method in which photometric measurement is performed at plural predetermined wavelengths, comprising:
    measuring an output variation due to a predetermined unit of variation for factors causing output variations at every predetermined wavelength;
    seeking a subspace which is orthogonal to respective variation vectors defined in a space having a dimension equal to the number of said predetermined wavelengths, each of said respective variation vectors having components corresponding to respective output variations at said wavelengths having been measured in said output variation step;
    performing photometric measurement for plural samples having known values of a physical or chemical target quantity, said photometric measurement comprising for each sample respectively, emitting light from a light source, passing said light into and out of each respective sample of said plural samples, sensing said passed light at respective plural predetermined wavelengths for each respective sample, and projecting vectors obtained on the subspace;
    calculating a calibration curve using said data obtained in the photometric measurement step, said calibration curve representing a correction of said target quantity with said data.

2. The spectrometric method as claimed in claim 1, in which said subspace is defined by base vectors which are orthogonal to all variation vectors defined in said subspace seeking step.

3. The spectrometric method as claimed in claim 1, in which variation vectors include at least sample temperature variation vector, sample scattering variation vector and machine temperature variation vector.

4. The spectrometric method as claimed in claim 1, further comprising:
    performing photometric measurement for an unknown sample at said plural predetermined wavelengths to obtain photometric data of said unknown sample, the photometric measurement of the unknown sample comprising emitting light from a light source, passing said light in said unknown sample, and sensing said passed light at said plural predetermined wavelengths to obtain said photometric data of said unknown sample;
    projecting a vector having components corresponding to said unknown sample photometric data on said subspace to convert said vector to data free from error variation factors; and
    calculating the target quantity using said data free from error variation factors according to said calibration curve determined in said calibration curve calculating step.

* * * * *